United States Patent [19]  [11] 4,304,916
Walker  [45] Dec. 8, 1981

[54] PROCESS OF MANUFACTURING HERBICIDAL ACTIVE SULFOXIDES AND SULFONE DERIVATIVES

[75] Inventor: Francis H. Walker, Mill Valley, Calif.

[73] Assignee: Stauffer Chemical Company, Westport, Conn.

[21] Appl. No.: 722,457

[22] Filed: Sep. 13, 1976

Related U.S. Application Data

[63] Continuation of Ser. No. 576,928, May 12, 1975, abandoned, which is a continuation-in-part of Ser. No. 391,387, Aug. 24, 1973, abandoned, which is a continuation of Ser. No. 280,381, Aug. 14, 1972, abandoned.

[51] Int. Cl.$^3$ ............................................. C07D 401/12
[52] U.S. Cl. .................................... 546/275; 546/336
[58] Field of Search .................. 260/294.8 F, 294.8 E; 546/275

[56] References Cited

U.S. PATENT DOCUMENTS 3,679,691  7/1972  Morrison et al. ............ 260/294.8 F
3,772,307 11/1973  Kaminsky et al. ........... 260/294.8 F

OTHER PUBLICATIONS

Klingsberg, Pyridine and its Derivatives, Part Two, Interscience, pp. 100–103, (1961).

*Primary Examiner*—Alan L. Rotman
*Attorney, Agent, or Firm*—Edwin H. Baker

[57] ABSTRACT

A process for manufacturing sulfoxide compounds is described herein. The process involves the reaction of certain thiocarbamic acid esters with an oxidizing agent at reduced temperatures.

2 Claims, No Drawings

PROCESS OF MANUFACTURING HERBICIDAL ACTIVE SULFOXIDES AND SULFONE DERIVATIVES

CROSS-REFERENCE TO RELATED APPLICATION

This is a continuation, of application Ser. No. 576,928, filed May 12, 1975 now abandoned which is a continuation-in-part of application Ser. No. 391,387, filed Aug. 24, 1973, now abandoned, which in turn is a continuation of application Ser. No. 280,381, filed Aug. 14, 1972, now abandoned.

DESCRIPTION OF THE INVENTION

This invention is directed to a novel group of compounds which may be generally described as sulfoxide derivatives of thiocarbamates which are highly active herbicides. These compounds are represented by the generic formula:

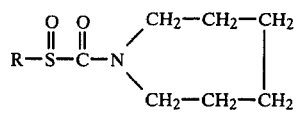

wherein R can be selected from pyridylmethyl.

The above-noted compounds can be prepared by reacting an oxidizing agent such as peracetic acid or m-chloroperoxybenzoic acid with a thiocarbamate compound corresponding to the following formula:

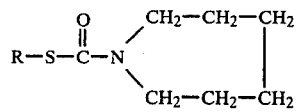

wherein R has been defined above. The reaction is carried out in the presence of a solvent such as chloroform, methylene chloride, benzene or toluene, and at a reduced temperature of from about −25° C. to about 15° C. The amount of oxidizing agent used must be at least one molar equivalent to form the sulfoxide derivative.

The thiocarbamate compounds are known herbicides and their method of synthesis is known; see U.S. Pat. Nos. 2,913,327; 2,983,747; 3,133,947; 3,175,897; and, 3,185,720, for example.

In order to illustrate the merits of the present invention, the following examples are provided:

EXAMPLE 1

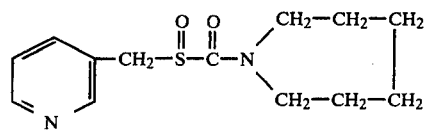

A solution was formed containing 11.0 grams (0.044 mole) S-(3-pyridylmethyl)-1-hexahydro-1H-azepine-1-carbothioate dissolved in 200 cc. of methylene chloride. This solution was cooled to −15° C. in a dry ice bath. Then, 9.0 grams (0.044 mole) of m-chloroperoxybenzoic acid was added portionwise over a period of 1.5 minutes. The mixture was stirred for 1 hour and the temperature was raised to 5° C. and held for 0.5 hours. Then, the mixture was warmed to room temperature. The reaction mixture was transferred to a separatory funnel and treated 4 times with 50 milliliters of a 5% sodium carbonate solution followed by two 50 milliliter water washes. After drying over MgSO₄, the solvent was removed by vacuum to yield 8.3 grams of product, $n_D^{30}$-1.5762.

Other compounds were prepared in an analogous manner starting with the appropriate starting materials as outlined above. The following is a table of compounds representative of those embodied by the present invention. Compound numbers have been assigned to them and are used for identification throughout the balance of the specification.

TABLE I $$\begin{array}{c} O\ O \\ \| \ \| \\ R-S-C-N \end{array} \Big\langle \begin{array}{c} CH_2-CH_2-CH_2 \\ | \\ CH_2-CH_2-CH_2 \end{array}$$

| Compound Number | R |
|---|---|
| 1 | -CH₂-(3-pyridyl) |
| 2 | -CH₂-(4-pyridyl) |

HERBICIDAL SCREENING TESTS

As previously mentioned, the novel compounds herein described are phytotoxic compounds which are useful and valuable in controlling various plant species. Compounds of this invention are tested as herbicides in the following manner.

PRE-EMERGENCE HERBICIDE SCREENING TEST

Using an analytical balance, 20 mg. of the compound to be tested is weighed out on a piece of glassine weighing paper. The paper and compound are placed in a 30 ml. wide-mouth bottle and 3 ml. of acetone containing 1% Tween 20 ® is added to dissolve the compound. If the material is not soluble in acetone, another solvent such as water, alcohol or dimethylformamide (DMF) is used instead. When DMF is used, only 0.5 ml. or less is used to dissolve the compound and then another solvent is used to make the volume up to 3 ml. The 3 ml. of solution is sprayed uniformly on the soil contained in a small Styrofoam flat one day after planting weed seeds in the flat of soil. A No. 152 DeVilbiss atomizer is used to apply the spray using compressed air at a pressure of 5 lb./sq. inch. The rate of application is 8 lb./acre and the spray volume is 143 gal./acre.

On the day preceding treatment, the Styrofoam flat, which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), yellow foxtail (*Setaria glauca*), watergrass (*Echinochloa crusgalli*), red oat (*Avena sativa*), redroot pigweed (*Amaranthus*

*retroflexus*), Indian mustard (*Brassica juncea*) and curly dock (*Rumex crispus*). Ample seeds are planted to give about 20 to 50 seedlings per row after emergence depending on the size of the plants.

After treatment, the flats are placed in the greenhouse at a temperature of 70° to 85° F. and watered by sprinkling. Two weeks after treatment the degree of injury or control is determined by comparison with untreated check plants of the same age. The injury rating from 0 to 100% is recorded for each species as percent control with 0% representing no injury and 100% representing complete kill.

POST-EMERGENCE HERBICIDE SCREENING TEST

Seeds of six plant species, including hairy crabgrass, watergrass, red oat, mustard, curly dock and Pinto beans (*Phaseolus vulgaris*) are planted in the Styrofoam flats as described above for pre-emergence screening. The flats are placed in the greenhouse at 70° to 85° F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg. of the test compound, dissolving it in 5 ml. of acetone containing 1% Tween ® and then adding 5 ml. of water. The solution is sprayed on the foliage using a No. 152 DeVilbiss atomizer at an air pressure of 5 lb./sq. inch. The spray concentration is 0.2% and the rate is 8 lb./acre. The spray volume is 476 gal./acre.

Injury ratings are recorded 14 days after treatment. The rating system is the same as described above for the pre-emergence test.

The results of these tests are shown in Table II.

TABLE II

| HERBICIDAL ACTIVITY - SCREENING RESULTS | | |
|---|---|---|
| Compound | Percent Control* at 8 lb/A | |
| Number | Preemergence | Postemergence |
| 1 | 63 | 27 |
| 2 | 43 | 23 |

*Average for seven plant species in the preemergence test and for six plant species in the postemergence test.

The compounds of the present invention can be used in any convenient form. Thus, the compounds can be made into emulsifiable liquids, emulsifiable concentrates, liquid, wettable powder, powders, granular or any other convenient form, and applied to the soil to control the undesired vegetation.

What is claimed is:

1. A process of manufacturing a pesticidal active compound having the following formula:

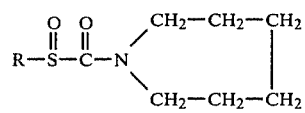

wherein R is selected from pyridylmethyl, comprising the steps of:
(a) combining an oxidizing agent and a thiocarbamate compound in an inert solvent system, said thiocarbamate having the following formula:

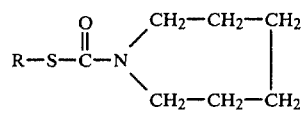

wherein R has been defined above;
(b) maintaining the temperature between −25° C. and 15° C.; and,
(c) said oxidizing agent being present in an amount of at least one molar equivalent.

2. The process of claim 1 wherein the following agent is selected from peracetic acid and m-chloroperoxybenzoic acid.

* * * * *